(12) United States Patent
Fusamae

(10) Patent No.: US 10,386,317 B2
(45) Date of Patent: Aug. 20, 2019

(54) MOISTURE DETECTING APPARATUS, MOISTURE DETECTING METHOD, AND NON-TRANSITORY COMPUTER READABLE STORAGE MEDIUM THAT STORES THEREIN MOISTURE DETECTION PROGRAM

(71) Applicants: ICHIGO HOLDINGS Co., Ltd., Miyagi (JP); Hideko Fusamae, Fukuoka (JP)

(72) Inventor: Tomoaki Fusamae, Suita (JP)

(73) Assignees: ICHIGO HOLDINGS Co., Ltd., Miyagi (JP); Hideko Fusamae, Fukuoka (JP)

(*) Notice: Subject to any disclaimer, the term of this patent is extended or adjusted under 35 U.S.C. 154(b) by 284 days.

(21) Appl. No.: 15/313,326

(22) PCT Filed: Jul. 22, 2015

(86) PCT No.: PCT/JP2015/070871
§ 371 (c)(1),
(2) Date: Nov. 22, 2016

(87) PCT Pub. No.: WO2016/017507
PCT Pub. Date: Feb. 4, 2016

(65) Prior Publication Data
US 2017/0199142 A1    Jul. 13, 2017

(30) Foreign Application Priority Data
Jul. 29, 2014  (JP) .................. 2014-154013

(51) Int. Cl.
*G01N 27/04* (2006.01)
*G01V 3/06* (2006.01)
*G01V 3/38* (2006.01)

(52) U.S. Cl.
CPC ............ *G01N 27/048* (2013.01); *G01V 3/06* (2013.01); *G01V 3/38* (2013.01); *Y02A 90/342* (2018.01)

(58) Field of Classification Search
None
See application file for complete search history.

(56) References Cited

FOREIGN PATENT DOCUMENTS

JP     2011-112357 A      6/2011
JP      2011112357 A  *   6/2011  ............ G01V 3/02

OTHER PUBLICATIONS

Machine Translation of JP-2011112357A, Yoshida H, Jun. 9, 2011.*
International Search Report issued in PCT/JP2015/070871; dated Oct. 20, 2015.

* cited by examiner

*Primary Examiner* — Jermele M Hollington
*Assistant Examiner* — Suresh K Rajaputra
(74) *Attorney, Agent, or Firm* — Studebaker & Brackett PC

(57) ABSTRACT

A moisture detecting apparatus includes a pair of current electrodes, a pair of potential electrodes, a frequency allotting section, a resistivity calculating section, and an estimation section. The frequency allotting section allots frequencies at regular frequency intervals ΔF in a range between first and second frequencies F1 and F2 (>F1) to a frequency of an alternating current. Each time a frequency is allotted, the resistivity calculating section calculates a resistivity value ρ in a predetermined region of the ground using a current value A detected by the current electrodes and a voltage value V detected by the potential electrodes. The estimation section obtains a maximum value ρ1 and a minimum value ρ2 among resistivity values ρ and estimates such that the smaller a quotient (ρ1/ρ2) obtained by dividing (Continued)

the maximum value ρ1 by the minimum value ρ2 is, the more moisture the predetermined region contains.

16 Claims, 11 Drawing Sheets

MOISTURE DETECTING APPARATUS, MOISTURE DETECTING METHOD, AND NON-TRANSITORY COMPUTER READABLE STORAGE MEDIUM THAT STORES THEREIN MOISTURE DETECTION PROGRAM

TECHNICAL FIELD

The present invention relates to a moisture detecting apparatus, a moisture detecting method, and a moisture detection program for detecting moisture contained in a predetermined region of the ground.

BACKGROUND ART

A traditional technique of detecting moisture contained in a predetermined region of the ground has been known. For example, a device has been disclosed that detects a water vein through change in distance among and position of four electrodes in dipole-dipole configuration by selection therefrom using a switch (see Patent Literature 1).

Patent Literature 1 discloses a water vein detecting device including a plurality of current electrode pairs, a plurality of potential electrode pairs, a first calculation means, a second calculation means, and an estimation means. The plurality of current electrode pairs each measure a current of an alternating current input to a predetermined region of the ground. The plurality of potential electrode pairs each measure a voltage corresponding to the alternating current. The first calculation means calculates a first resistivity value indicating a resistivity in the predetermined region of the ground using a current and a voltage based on an alternating current having a first frequency. The second calculation means calculates a second resistivity value indicating a resistivity in the predetermined region of the ground using a current and a voltage based on an alternating current having a second frequency higher than the first frequency. When the second resistivity value is larger than the first resistivity value and a difference therebetween is at least a specific value, the estimation means estimates that the predetermined region of the ground includes a water vein.

It is also disclosed that the above water vein detecting device detects a water vein in the same region of the ground based on two types of resistivity values obtained from the alternating currents having the different two frequencies, thereby enabling achievement of highly accurate detection of a water vein.

CITATION LIST

Patent Literature

[Patent Literature 1] Japanese Patent Application Laid-Open Publication No. 2011-112357

SUMMARY OF INVENTION

Technical Problem

However, it may be difficult to appropriately set the first and second frequencies in the water vein detecting device of Patent Literature 1. In other words, the first and second frequencies have been set based on experiences of skilled engineers.

A moisture detecting apparatus, a moisture detecting method, and a moisture detection program according to the present invention have been made in view of the foregoing problem and have an object of detecting moisture contained in the ground with high accuracy without relying upon the skilled engineers.

Solution to Problem

A moisture detecting apparatus according to the present invention is a moisture detecting apparatus that detects moisture contained in a predetermined region of a ground. The moisture detecting apparatus includes plural pairs of current electrodes, plural pairs of potential electrodes, a frequency allotting means, a resistivity calculating means, and an estimation means. The plural pairs of current electrodes each measure a current value of an alternating current input to the predetermined region. The plural pairs of potential electrodes each measure a voltage value corresponding to the alternating current. The frequency allotting means allots a plurality of frequencies at specific frequency intervals in a range between a preset first frequency and a second present frequency higher than the first frequency to a frequency of the alternating current. The resistivity calculating means calculates a resistivity value in the predetermined region using the current value and the voltage value each time a frequency is allotted by the frequency allotting means. The estimation means obtains a maximum value and a minimum value among resistivity values obtained through calculation by the resistivity calculating means and performs estimation such that the smaller a quotient obtained by dividing the maximum value by the minimum value is, the more moisture the predetermined region contains.

A moisture detecting apparatus according to the present invention is a moisture detecting apparatus that detects moisture contained in a predetermined region of the ground. The moisture detecting apparatus includes plural pairs of current electrodes, plural pairs of potential electrodes, a frequency allotting means, a resistivity calculating means, a deviation calculating means, and a frequency band selecting means. The plural pairs of current electrodes each measure a current value of an alternating current input to the predetermined region. The plural pairs of potential electrodes each measure a voltage value corresponding to the alternating current. The frequency allotting means allots a plurality of frequencies at specific frequency intervals in a range between a preset third frequency and a fourth frequency higher than the third frequency to a frequency of the alternating current. The resistivity calculating means calculates a resistivity value in the predetermined region using the current value and the voltage value each time a frequency is allotted by the frequency allotting means. The deviation calculating means divides the range between the third and fourth frequencies into two or more frequency band zones and calculates, in each of the frequency band zones, a standard deviation of resistivity values obtained through calculation by the resistivity calculating means. The frequency band selecting means selects, as a frequency for use in detection of moisture contained in the ground, a frequency band corresponding to one of the frequency band zones of which standard deviation is a maximum among standard deviations obtained through calculation by the deviation calculating means.

A moisture detecting method according to the present invention uses a moisture detecting apparatus that detects moisture contained in a predetermined region of a ground. The moisture detecting apparatus includes plural pairs of current electrodes that each measure a current value of an alternating current input to the predetermined region and plural pairs of potential electrodes that each measure a voltage value corresponding to the alternating current. The method includes allotting a plurality of frequencies, calculating a resistivity value, and performing estimation. In the allotting a plurality of frequencies, a plurality of frequencies at specific frequency intervals in a range between a preset first frequency and a second frequency higher than the first frequency are allotted to a frequency of the alternating current. In the calculating a resistivity value, a resistivity value of a resistivity in the predetermined region is calculated using the current value and the voltage value each time a frequency is allotted in the allotting a plurality of frequencies. In the performing estimation, a maximum value and a minimum value among resistivity values obtained through the calculating a resistivity value are obtained and estimation is performed such that the smaller a quotient obtained by dividing the maximum value by the minimum value is, the more moisture the predetermined region contains.

A moisture detecting method according to the present invention uses a moisture detecting apparatus that detects moisture contained in a predetermined region of a ground. The moisture detecting apparatus includes plural pairs of current electrodes that each measure a current value of an alternating current input to the predetermined region and plural pairs of potential electrodes that each measure a voltage value corresponding to the alternating current. The method includes allotting a plurality of frequencies, calculating a resistivity value, calculating a deviation, and selecting a frequency band. In the allotting a plurality of frequencies, a plurality of frequencies at specific frequency intervals in a range between a preset third frequency and a fourth frequency higher than the third frequency are allotted to a frequency of the alternating current. In the calculating a resistivity value, a resistivity value in the predetermined region is calculated using the current value and the voltage value each time a frequency is allotted in the allotting a plurality of frequencies. In the calculating a deviation, the range between the third and fourth frequencies is divided into two or more frequency band zones and a standard deviation of resistivity values obtained through the calculating a resistivity value is calculated in each of the frequency band zones. In the selecting a frequency band, a frequency band corresponding to one of the frequency band zones of which standard deviation is a maximum among standard deviations obtained through the calculating a deviation is selected as a frequency for use in detection of moisture contained in the ground.

A moisture detection program according to the present invention is a moisture detection program for a moisture detecting apparatus that detects moisture contained in a predetermined region of a ground. The moisture detecting apparatus includes plural pairs of current electrodes that each measure a current value of an alternating current input to the predetermined region, plural pairs of potential electrodes that each measure a voltage value corresponding to the alternating current, and a computer. The program causes the computer to function as a frequency allotting means, a resistivity calculating means, and an estimation means. The frequency allotting means allots a plurality of frequencies at specific frequency intervals in a range between a preset first frequency and a second frequency higher than the first frequency to a frequency of the alternating current. The resistivity calculating means calculates a resistivity value in the predetermined region using the current value and the voltage value each time a frequency is allotted by the frequency allotting means. The estimation means obtains a maximum value and a minimum value among resistivity values obtained through calculation by the resistivity calculating means and performs estimation such that the smaller a quotient obtained by dividing the maximum value by the minimum value is, the more moisture the predetermined region contains.

A moisture detection program according to the present invention is a moisture detection program for a moisture detecting apparatus that detects moisture contained in a predetermined region of a ground. The moisture detecting apparatus includes plural pairs of current electrodes that each measure a current value of an alternating current input to the predetermined region, plural pairs of potential electrodes that each measure a voltage value corresponding to the alternating current, and a computer. The program causes the computer to function as a frequency allotting means, a resistivity calculating means, a deviation calculating means, and a frequency band selecting means. The frequency allotting means allots a plurality of frequencies at specific frequency intervals in a range between a preset third frequency and a fourth frequency higher than the third frequency to a frequency of the alternating current. The resistivity calculating means calculates a resistivity value in the predetermined region using the current value and the voltage value each time a frequency is allotted by the frequency allotting means. The deviation calculating means divides the range between the third and fourth frequencies into two or more frequency band zones and calculates, in each of the frequency band zones, a standard deviation of resistivity values obtained through calculation by the resistivity calculating means. The frequency band selecting means selects, as a frequency for use in detection of moisture contained in the ground, a frequency band corresponding to one of the frequency band zones of which standard deviation is a maximum among standard deviation obtained through calculation by the deviation calculating means.

Advantageous Effects of Invention

The moisture detecting apparatus, the moisture detecting method, and the moisture detection program according to the present invention can achieve highly accurate detection of much moisture being contained in the ground even by a person other than a skilled engineer.

BRIEF DESCRIPTION OF DRAWINGS

FIG. 1A illustrates principles of a dipole-dipole method. FIG. 1B illustrates a measurable region.

FIG. 2A is a block diagram illustrating overall configuration of the moisture detecting apparatus. FIG. 2B is a functional block diagram of a computer illustrated in FIG. 2A.

FIG. 5A is a perspective view indicating a shape and a size of a water container. FIG. 5B is a cross-sectional view illustrating a state in which the water container illustrated in FIG. 5A is buried in the ground and measurement points at which the moisture detecting apparatus performs measurement.

FIG. 7A is a graph representation indicating a relationship between frequency and resistivity where a moisture content in the water container is 60%. FIG. 7B is a graph representation indicating a relationship between frequency and resistivity where a moisture content in the water container is 70%. FIG. 7C is a graph representation indicating a relationship between frequency and resistivity where a moisture content in the water container is 80%.

FIG. 8A indicates a standard deviation distribution in a frequency band of 1 Hz to 20 Hz. FIG. 8B indicates a standard deviation distribution in a frequency band of 21 Hz to 40 Hz. FIG. 8C indicates a standard deviation distribution in a frequency band of 41 Hz to 60 Hz. FIG. 8D indicates a standard deviation distribution in a frequency band of 61 Hz to 80 Hz. FIG. 8E indicates a standard deviation distribution in a frequency band of 81 Hz to 100 Hz. FIG. 8F indicates standard deviation ranges.

DESCRIPTION OF EMBODIMENTS

The following describes a moisture detecting apparatus according to an embodiment of the present invention with reference to the accompanying drawings. However, the present invention is not limited to the following embodiment.

<Principles for Obtaining Resistivity Value ρ in Ground>

Figure 1A:
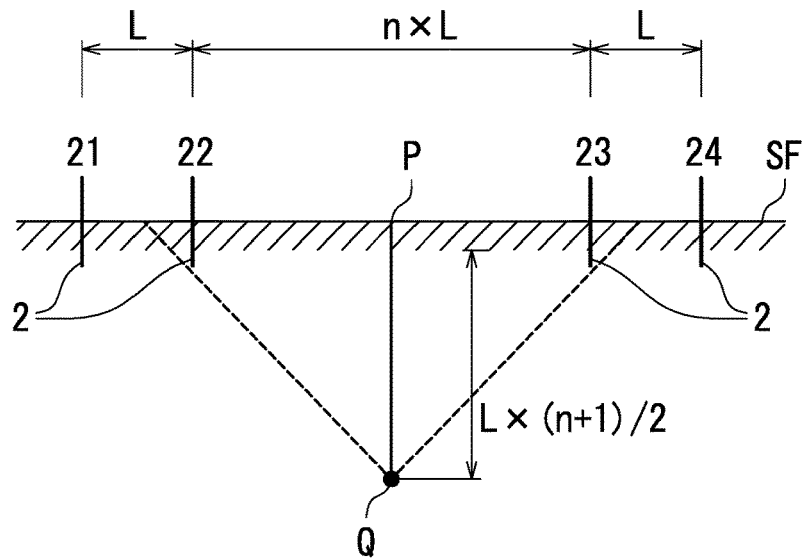
FIGS. 1A and 1B are diagrams illustrating principles for measurement by a moisture detecting apparatus according to an embodiment of the present invention.
Figure 1B:
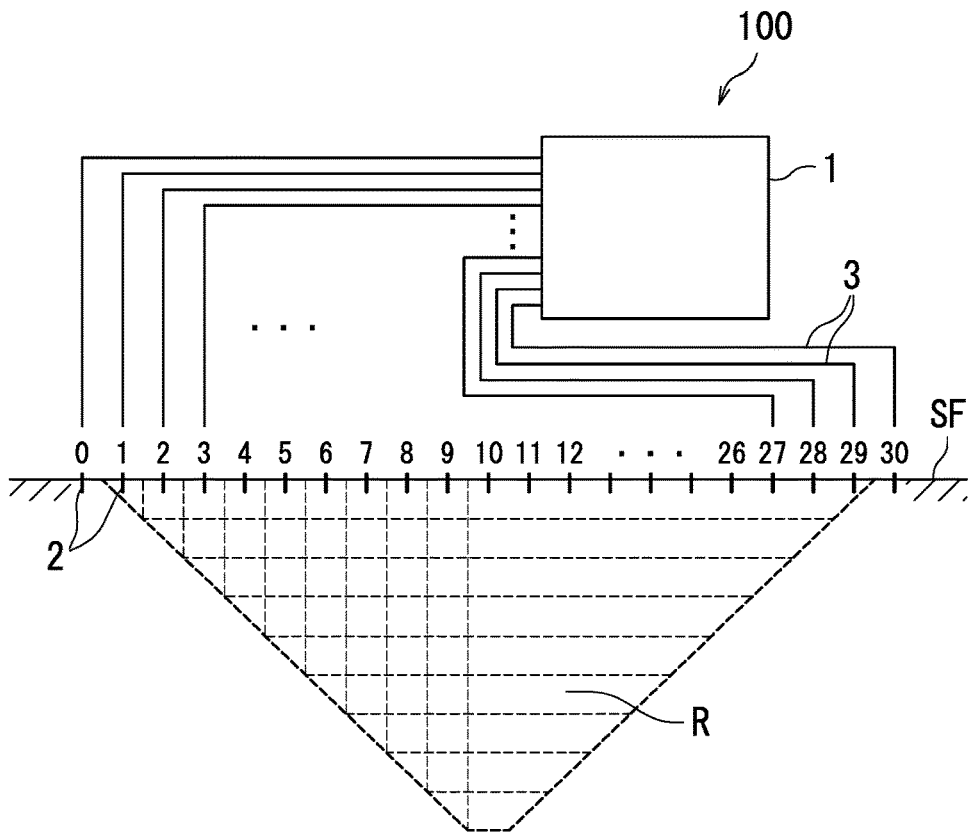

A moisture detecting apparatus 100 according to an embodiment of the present invention will be described first with reference to FIGS. 1A and 1B. FIG. 1A is a diagram illustrating principles of a dipole-dipole method adopted in the moisture detecting apparatus 100 according to the embodiment of the present invention. FIG. 1B illustrates overall configuration of the moisture detecting apparatus 100 and indicates a measurable region and measurement points MP.

As illustrated in FIG. 1A, the moisture detecting apparatus 100 includes a pair of current electrodes 21 and 22 and a pair of potential electrodes 23 and 24. The current electrodes 21 and 22 each are partially buried in a ground surface SF at a distance L therebetween. In a similar manner, the potential electrodes 23 and 24 each are partially buried in the ground surface SF at the distance L therebetween. A distance between the current electrode 22 and the potential electrode 23 herein is set at an integral multiple (n times herein) of the distance L. In such a configuration, a resistivity value ρ at a point Q located at a depth of (L×(n+1)/2) from a midpoint P on the ground surface SF between the current electrode 22 and the potential electrode 23 can be detected using the following equation (1).

$$\rho = n \times (n+1) \times (n+2) \times \pi \times L \times (V/A) \quad (1)$$

Here, a voltage value V is a value of a voltage detected by the pair of potential electrodes 23 and 24 and a current value A is a value of a current detected by the pair of current electrodes 21 and 22.

As illustrated in FIG. 1B, the moisture detecting apparatus 100 includes a moisture detection device main body 1, electrodes 2, and lead wires 3. The electrodes 2 are partially buried in the ground surface SF at intervals of the distance L and function as the current electrodes 21 and 22 or the potential electrodes 23 and 24. A plurality of electrodes 2 are provided. Thirty-one electrodes 2 are provided herein. The lead wires 3 connect the electrodes 2 to the moisture detection device main body 1 in a conductive manner. Specifically, the lead wires 3 connect the electrodes 2 to an electrode switching circuit 14, which will be described later with reference to FIG. 2A, in a conductive manner. The moisture detection device main body 1 sets, via the lead wires 3, two of the thirty-one electrodes 2 as the pair of current electrodes 21 and 22 and another two thereof as the pair of potential electrodes 23 and 24. Further, as illustrated in FIG. 1B, a trapezoidal region R indicated by a thick broken line under the ground surface SF is a detectable region in which the moisture detecting apparatus 100 is capable of performing detection. Note that one (an upper base) of the bases of the trapezoidal region R is located on the ground surface SF and is a segment connecting a midpoint of two electrodes at the left end and a midpoint of two electrodes at the right end.

<Hardware Configuration of Moisture Detection Device Main Body 1>

Figure 2A:
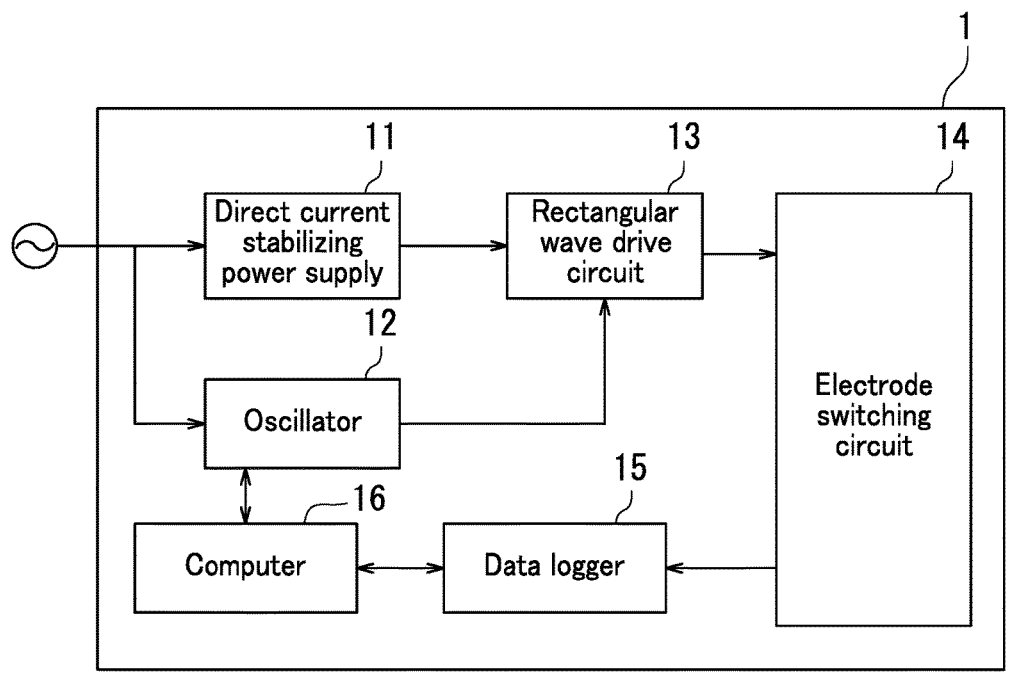
FIGS. 2A and 2B each are a block diagram illustrating configuration of the moisture detecting apparatus according to the embodiment of the present invention.
Figure 2B:
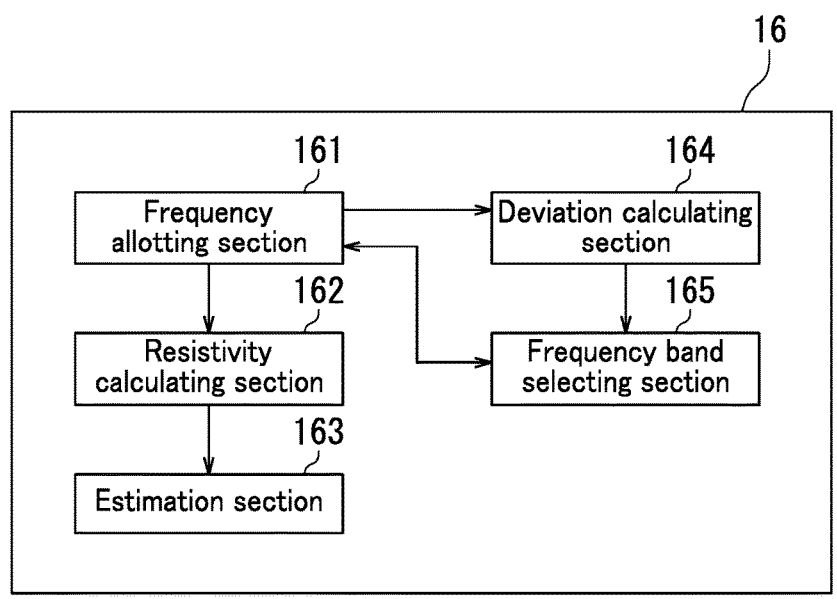

Configuration of the moisture detection device main body 1 will be described next with reference to FIGS. 2A and 2B. FIG. 2A is a block diagram illustrating overall configuration of the moisture detection device main body 1. FIG. 2B is a functional block diagram of a computer 16 illustrated in FIG. 2A. As illustrated in FIG. 2A, the moisture detection device main body 1 includes a direct current stabilizing power supply 11, an oscillator 12, a rectangular wave drive circuit 13, an electrode switching circuit 14, a data logger 15, and the computer 16.

The direct current stabilizing power supply 11 generates a direct current (having for example 1.3 amperes herein) from a commercially available power supply having an alternating current of 100 V and outputs the generated direct current. The oscillator 12 outputs alternating current signals having a frequency of 1 Hz to 100 Hz in response to an instruction from the computer 16. The rectangular wave drive circuit 13 outputs a rectangular wave current at a frequency of Fα Hz using the direct current input from the direct current stabilizing power supply 11 and the alternating current signals (at a frequency of Fα Hz herein for the sake of convenience) input from the oscillator 12. The electrode switching circuit 14 sets two electrodes among the thirty-one electrodes 2 illustrated in FIG. 1B as the pair of current electrodes 21 and 22 and another two electrodes thereamong as the pair of potential electrodes 23 and 24. Furthermore, the electrode switching circuit 14 applies the rectangular wave current at a frequency of Fα Hz (having a current value A), which is input from the rectangular wave drive circuit 13, to the set pair of current electrodes 21 and 22. In addition, the electrode switching circuit 14 detects a voltage value V from the set pair of potential electrodes 23 and 24.

The data logger 15 stores therein identification information that identifies the pair of current electrodes 21 and 22, the current value A of the rectangular wave current applied to the pair of current electrodes 21 and 22, identification information that identifies the pair of potential electrodes 23 and 24, and the voltage value V detected from the pair of potential electrodes 23 and 24. The pair of current electrodes 21 and 22 and the pair of potential electrodes 23 and 24 herein are set by the electrode switching circuit 14. Furthermore, the data logger 15 stores the above four items of information each specific time period (for example, 10 msec.) preset in advance.

The computer 16 acquires, from the oscillator 12, a frequency F of the rectangular wave current applied to the pair of current electrodes 21 and 22. The computer 16 further acquires, from the data logger 15, the identification information that identifies the pair of current electrodes 21 and 22, the identification information that identifies the pair of potential electrodes 23 and 24, the current value A of the rectangular wave current applied to the pair of current electrodes 21 and 22, and the voltage value V detected from the pair of potential electrodes 23 and 24. Furthermore, the computer 16 assigns an oscillation frequency for the oscillator 12. In addition, the computer 16 implements functional sections indicated in FIG. 2B.

<Functional Configuration of Moisture Detection Device Main Body 1>

The computer 16 includes a central processing unit (CPU), a read only memory (ROM), a random access memory (RAM), and a hard disk drive (HDD). The ROM (or the HDD) stores therein control programs including a moisture detection program according to the present invention. The CPU reads out and executes the moisture detection program stored in the ROM (or the HDD) to function as various functional sections including a frequency allotting section 161, a resistivity calculating section 162, an estimation section 163, a deviation calculating section 164, and a frequency band selecting section 165. The CPU uses the RAM as a work area during execution of the moisture detection program.

Figure 4:
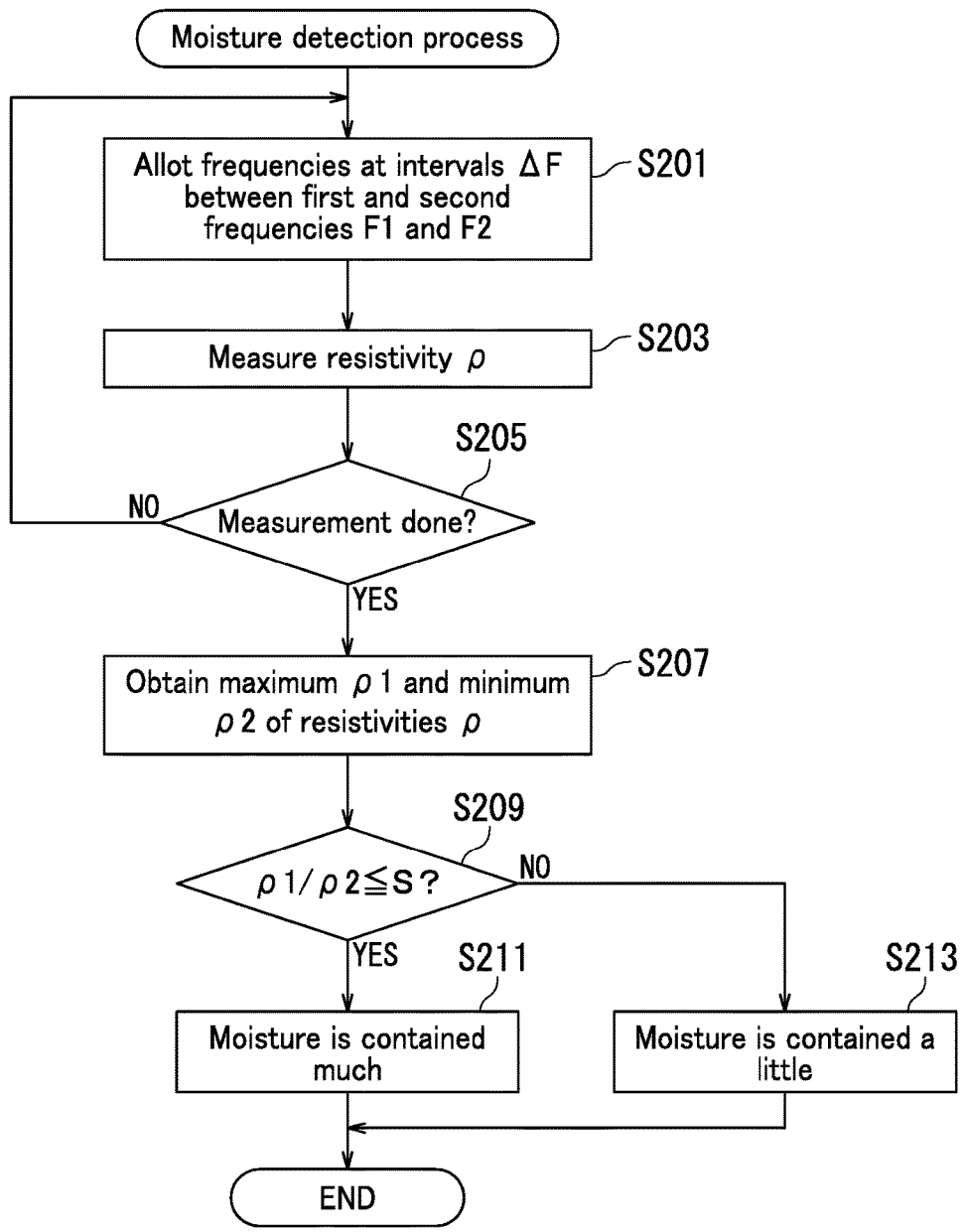
FIG. 4 is a flowchart depicting steps of a moisture detection process performed by the moisture detecting apparatus illustrated in FIG. 2A.

In a situation in which a "moisture detection process" depicted in FIG. 4 is executed, the frequency allotting section 161 allots a plurality of frequencies at regular frequency intervals $\Delta F$ in a range between a preset first frequency F1 and a second frequency F2 higher than the first frequency F1 to the frequency $F\alpha$ of an alternating current (the rectangular wave current herein) applied to the pair of current electrodes 21 and 22. The frequency allotting section 161 herein corresponds to an example of a "frequency allotting means". The frequency intervals $\Delta F$ correspond to an example of "specific frequency intervals". The present embodiment describes a configuration in which the first and second frequencies F1 and F2 are 21 Hz and 40 Hz, respectively, and the frequency intervals $\Delta F$ each are 1 Hz. That is, the frequency allotting section 161 in the present application allots a frequency every 1 Hz in a range between 21 Hz and 40 Hz. Note that the present embodiment describes a configuration in which the frequency allotting section 161 allots a plurality of frequencies at the regular frequency intervals $\Delta F$. However, the frequency allotting section 161 may allot a plurality of frequencies by another method.

Figure 3:
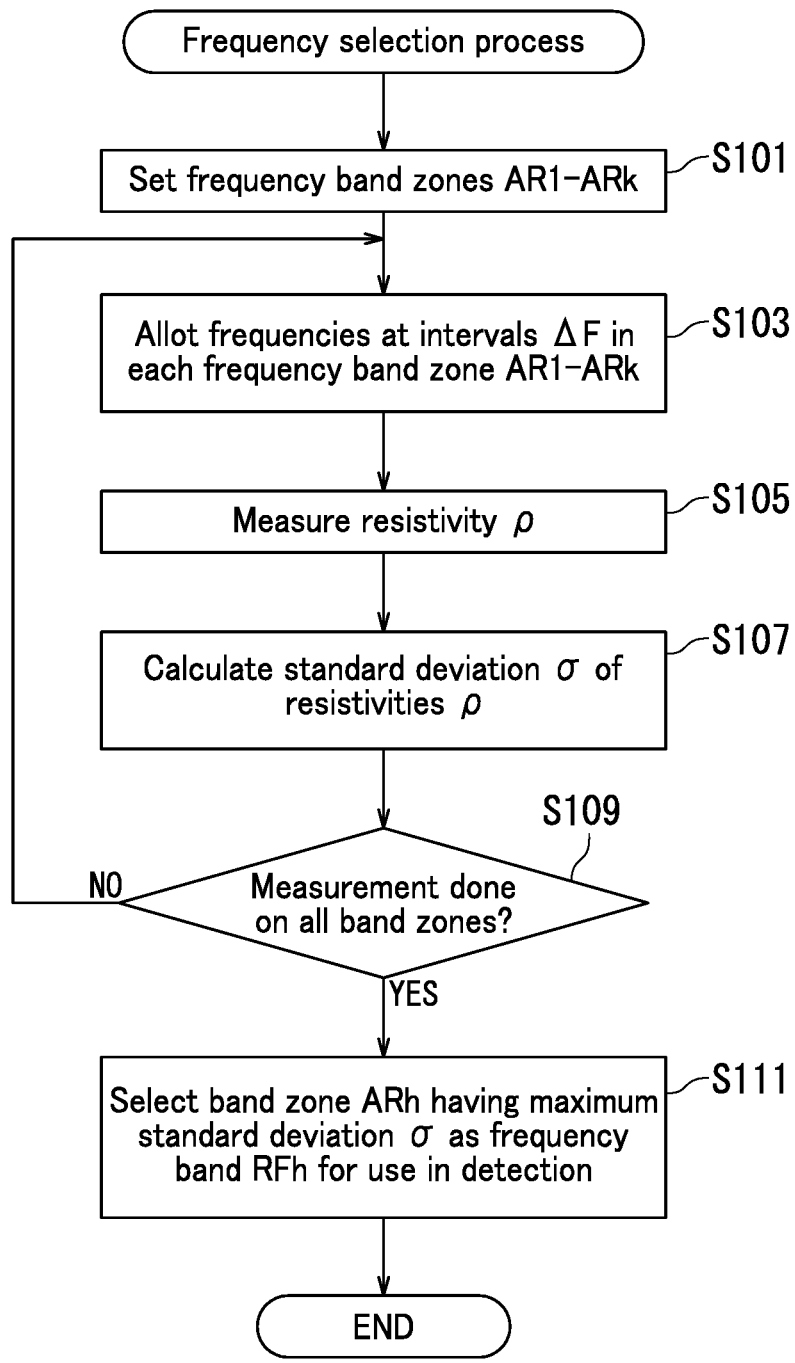
FIG. 3 is a flowchart depicting steps of a frequency selection process performed by the moisture detecting apparatus illustrated in FIG. 2A.

Furthermore, in a situation in which a "frequency selection process" depicted in FIG. 3 is executed, the frequency allotting section 161 allots a plurality of frequencies at the regular frequency intervals $\Delta F$ in a range between a third frequency F3 lower than the first frequency F1 and a fourth frequency F4 higher than the second frequency F2. The present embodiment describes a configuration in which the third and fourth frequencies F3 and F4 are 1 Hz and 100 Hz, respectively, and the frequency intervals $\Delta F$ each are 1 Hz. That is, the frequency allotting section 161 in the present embodiment allots a frequency every 1 Hz in a range between 1 Hz and 100 Hz.

Each time the frequency allotting section 161 allots a frequency to the frequency $F\alpha$, the resistivity calculating section 162 calculates a resistivity value $\rho$ that represents a resistivity in the predetermined region of the ground using the current value A of the rectangular wave current applied to the pair of current electrodes 21 and 22 and the voltage value V detected from the pair of potential electrodes 23 and 24. The resistivity calculating section 162 herein corresponds to an example of a "resistivity calculating means".

The rectangular wave current is applied to the pair of current electrodes 21 and 22 in the present embodiment. This means that a period in which a current having a maximum current value flows is long. Furthermore, an S/N ratio can be increased by increasing the current value. In this connection, the resistivity value $\rho$ can be detected highly accurately. Consequently, application of the rectangular wave current to the pair of current electrodes 21 and 22 can obtain an accurate resistivity value $\rho$.

The present embodiment describes a configuration in which the rectangular wave current is applied to the pair of current electrodes 21 and 22. However, it is only required that an alternating current is applied to the pair of current electrodes 21 and 22. For example, an alternating current having a sine wave form or a triangular wave form may be applied to the pair of current electrodes 21 and 22.

The estimation section 163 obtains a maximum value $\rho 1$ and a minimum value $\rho 2$ among calculated resistivity values $\rho$ and performs estimation such that the smaller a quotient ($\rho 1/\rho 2$) obtained by dividing the maximum value $\rho 1$ by the minimum value $\rho 2$ is, the more the predetermined region contains moisture. The estimation section 163 herein corresponds to an example of an "estimation means".

As will be described later with reference to FIG. 6, even when the frequency $F\alpha$ is changed in a range between 1 Hz and 100 Hz, a resistivity value $\rho$ in the predetermined region hardly varies in a situation in which the predetermined region contains water (a moisture content of 100%). Furthermore, as will be described later with reference to FIGS. 7A-7C, the more the predetermined region contains moisture, the smaller variation in resistivity value $\rho$ (variation corresponding to a deviation herein) where the frequency $F\alpha$ is changed in the range between 1 Hz and 100 Hz (particularly, where the frequency $F\alpha$ is changed in a range between 21 Hz and 40 Hz) is. As such, in a situation in which the frequency $F\alpha$ is changed in the range between 21 Hz and 40 Hz, it can be estimated such that the smaller a quotient ($\rho 1/\rho 2$) obtained by dividing the maximum value $\rho 1$ by the minimum value $\rho 2$ among the resistivity values $\rho$ is, the more the predetermined region contains moisture.

The frequency allotting section 161 in the present embodiment allots a frequency every 1 Hz in the range between 21 Hz ad 40 Hz to the frequency $F\alpha$ of the alternating current applied to the pair of current electrodes 21 and 22. In the above configuration, twenty frequencies are allotted and twenty resistivity values $\rho$ corresponding to the respective allotted twenty frequencies can accordingly be obtained. Consequently, the estimation section 163 can appropriately obtain the maximum value ρ1 and the minimum value ρ2.

In other words, it is preferable that the frequency intervals ΔF each are no greater than 1 Hz and the frequency allotting section 161 allots at least ten frequencies. The reason thereof is as follows. The estimation section 163 performs estimation such that the smaller the quotient (ρ1/ρ2) obtained by dividing the maximum value ρ1 by the minimum value ρ2 is, the more the predetermined region contains moisture. Therefore, it is essential to appropriately obtain the maximum value ρ1 and the minimum value ρ2. Therefore, it is preferable that the frequency intervals ΔF are small and the frequency allotting section 161 allots many (at least ten) frequencies.

The deviation calculating section 164 divides the range between the third and fourth frequencies F3 and F4 into two or more frequency band zones ARk and obtains, in each of the frequency band zones ARk, a standard deviation σ of the resistivity values ρ obtained through calculation by the resistivity calculating section 162. The deviation calculating section 164 herein corresponds to an example of a "deviation calculating means". As will be described later with reference to FIG. 7A, the present embodiment describes a configuration in which the range between 1 Hz that is the third frequency F3 and 100 Hz that is the fourth frequency F4 is equally divided into five frequency band zones ARk (k=1 to 5 herein). Note that standard deviations σ each corresponding to one of the frequency band zones ARk herein are represented by a standard deviation σk (k=1 to 5).

The frequency band selecting section 165 selects, as a frequency band FRh for use in detecting moisture contained in the ground, a frequency band FRh corresponding to one ARh of the frequency band zones of which standard deviation σ is a maximum among standard deviations σ obtained through calculation by the deviation calculating section 164. The frequency band selecting section 165 herein corresponds to an example of a "frequency band selecting means". In the present embodiment, a frequency band FR2 (21 Hz to 40 Hz) corresponding to a frequency band zone AR2 of which standard deviation σ is a maximum is selected as a frequency band FR2 for use in detecting moisture contained in the ground, as will be described later with reference to FIG. 7A.

In other words, among the frequencies allotted by the frequency allotting section 161, the first frequency F1 is a lower limit frequency (21 Hz) in the frequency band FRh (frequency band FR2 in the example illustrated in FIG. 7A) selected by the frequency band selecting section 165 and the second frequency F2 is an upper limit frequency (40 Hz) in the frequency band FRh (frequency band FR2 in the example illustrated in FIG. 7A) selected by the frequency band selecting section 165.

Allotment of the first and second frequencies F1 and F2 as above can enable appropriate setting of the frequency range in the moisture detection process depicted in FIG. 4. As a result, accurate determination as to whether or not much moisture is contained can be done in the moisture detection process.

<Operation of Moisture Detection Device Main Body 1>

With reference to FIG. 3, the frequency selection process will be described next. The frequency selection process herein means a process of frequency band selection as a frequency band FRh for use in detecting moisture contained in the ground. FIG. 3 is a flowchart depicting steps of the frequency selection process performed by the moisture detecting apparatus 100 illustrated in FIG. 2A. First, the range between the third frequency F3 (1 Hz herein) and the fourth frequency F4 (100 Hz herein) is divided into two or more (five herein) frequency band zones ARk (k=1 to 5 herein) by the deviation calculating section 164 (Step S101). Next, frequencies at the frequency intervals ΔF (1 Hz herein) in each of the frequency band zones ARk (k=1 to 5 herein) are allotted by the frequency allotting section 161 (Step S103). Step S103 herein corresponds to "allotting a plurality of frequencies".

Each time a frequency is allotted at Step S103, a resistivity ρ are calculated by the resistivity calculating section 162 (Step S105). Step S105 herein corresponds to an example of "calculating a resistivity". Subsequently, a standard deviation σ of the resistivity values ρ calculated through Step S105 is calculated by the deviation calculating section 164 (Step S107). Step S107 herein corresponds to an example of "calculating a deviation". Whether or not measurement has been done on all the frequency band zones ARk is then determined (Step S109).

When it is determined that measurement has been done on not all the frequency band zones (NO at Step S109), the routine returns to Step S103 and the following steps are executed. When it is determined that measurement has been done on all the frequency band zones ARk (YES at Step S109), a frequency band FRh corresponding to a frequency band zone ARh of which standard deviation σ is a maximum among standard deviations σ obtained through Step S107 is selected as a frequency band FRh for use in detecting moisture contained in the ground by the frequency band selecting section 165 (Step S111). The routine ends then. Step S111 herein corresponds to an example of "selecting a frequency".

As described above, the frequency band FRh corresponding to the frequency band zone ARh of which standard deviation σ is a maximum is selected as a frequency band FRh for use in detecting moisture contained in the ground. This can be selection of an appropriate frequency band FRh. In other words, a resistivity value ρ significantly varies when the frequency is changed in a frequency band FRh corresponding to a frequency band zone ARh of which standard deviation σ is a maximum. As such, the quotient (ρ1/ρ2) obtained by dividing the maximum value ρ1 by the minimum value ρ2 among the resistivity values ρ obtained through calculation by the estimation section 163 is large in a situation in which not so much moisture is contained in the ground. As a result, estimation by the estimation section 163 can be facilitated.

The present embodiment describes a configuration in which the frequency band selecting section 165 selects a frequency band FRh corresponding to a frequency band zone ARh of which standard deviation σ is a maximum as a frequency band FRh for use in detecting moisture in the ground. However, selection of a frequency band FRh may be made by another method. For example, the frequency band selecting section 165 may select a frequency band FRk in which dispersion in resistivity values ρ is large. Specifically, it is possible that a maximum value and a minimum value among resistivity values ρ in each frequency band FRk are obtained and a frequency band FRk having a maximum difference therebetween is selected. Alternatively, it is possible that a maximum value and a minimum value among resistivity values ρ in each frequency band FRk are obtained and a frequency band FRk having a maximum quotient of those obtained by dividing the maximum value by the minimum value is selected.

With reference to FIG. 4, the moisture detection process will be described next. The moisture detection process herein is a process of detecting whether or not much moisture is contained in the predetermined region of the ground. FIG. 4 is a flowchart depicting steps of the moisture detection process performed by the moisture detecting apparatus 100 illustrated in FIGS. 2A and 2B. First, frequencies at regular frequency intervals $\Delta F$ (1 Hz herein) in a range between the first frequency F1 (21 Hz herein) and the second frequency F2 (40 Hz herein) are allotted by the frequency allotting section 161 (Step S201). Step S201 herein corresponds to an example of "allotting a plurality of frequencies".

Each time a frequency is allotted at Step S201, a resistivity value $\rho$ is measured by the resistivity calculating section 162 (Step S203). Step S203 herein corresponds to an example of "calculating a resistivity". Next, whether or not measurement of a resistivity value $\rho$ has been done on all the allotted frequencies is determined (Step S205). When it is determined that measurement of a resistivity value $\rho$ has been done on not all of the frequencies (NO at Step S205), the routine returns to Step S201 and Step S201 and the following steps are executed. When it is determined that measurement of a resistivity value $\rho$ has been done on all of the frequencies (YES at Step S205), a maximum value $\rho 1$ and a minimum value $\rho 2$ among the resistivity values $\rho$ are obtained by the estimation section 163 (Step S207).

Subsequently, whether or not a quotient ($\rho 1/\rho 2$) obtained by dividing the maximum value $\rho 1$ by the minimum value $\rho 2$ is no greater than a preset threshold value S is determined by the estimation section 163 (Step S209). When it is determined that the quotient ($\rho 1/\rho 2$) is no greater than the threshold value S (YES at Step S209), it is estimated by the estimation section 163 that much moisture is contained in the predetermined region (Step S211). The routine then ends. When it is determined that the quotient ($\rho 1/\rho 2$) is larger than the threshold value S (NO at Step S209), it is estimated that not so much moisture is contained in the predetermined region (Step S213). The routine then ends. Steps S207 to S213 herein correspond to an example of "obtaining a maximum value and a minimum value and performing estimation".

When the quotient ($\rho 1/\rho 2$) is determined to be no greater than the threshold value S, the estimation section 163 estimates that much moisture is contained in the predetermined region of the ground. Estimation as above can achieve highly accurate detection of much moisture being contained in the ground even by a person other than a skilled engineer.

The present embodiment descries a configuration in which the smaller the quotient ($\rho 1/\rho 2$) obtained by dividing the maximum value $\rho 1$ by the minimum value $\rho 2$ is, the more moisture the estimation section 163 estimates that the predetermined region contains. However, it is only required that a configuration is made such that the smaller dispersion of resistivity values $\rho$ is, the more moisture the estimation section 163 estimates that the predetermined region contains. For example, a configuration may be made such that the smaller the standard deviation $\sigma$ of the resistivity values $\rho$ is, the more moisture the estimation section 163 estimates that the predetermined region contains. Alternatively, a configuration may be made for example such that the smaller a value (($\rho 1 - \rho 2$)/$\rho A$) obtained by dividing a difference obtained by subtracting the minimum value $\rho 2$ from the maximum value $\rho 1$ by an average value $\rho A$ of the resistivity values $\rho$ is, the more moisture the estimation section 163 estimates that the predetermined region contains.

<Experiment for Demonstrating Effects>

Figure 5A:
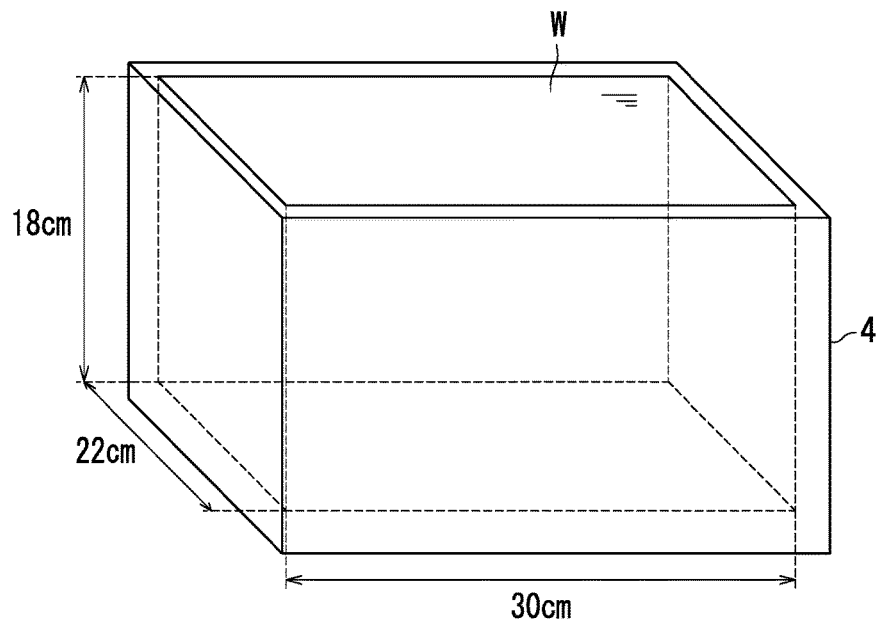
FIGS. 5A and 5B each illustrate an experimental method for demonstrating effects of the moisture detecting apparatus illustrated in FIG. 2A.

The following describes an experimental method for demonstrating effects of the moisture detecting apparatus 100 according to the present invention and experimental results with reference to FIGS. 5A-8F. FIGS. 5A and 5B illustrate an experimental method for demonstrating the effects of the moisture detecting apparatus illustrated in FIG. 2A. FIG. 5A is a perspective view indicating a shape and a size of a water container 4. FIG. 5B is a cross-sectional view illustrating a state in which the water container 4 illustrated in FIG. 5A is buried in the ground and measurement points at which the moisture detecting apparatus 100 performs measurement.

As illustrated in FIG. 5A, the water container 4 is in a rectangular parallelepiped shape having, as inner dimensions, a width of 30 cm, a length of 22 cm, and a height of 18 cm. Water or a mixture of water and volcanic ash sandy soil is put into the water container 4.

Figure 5B:
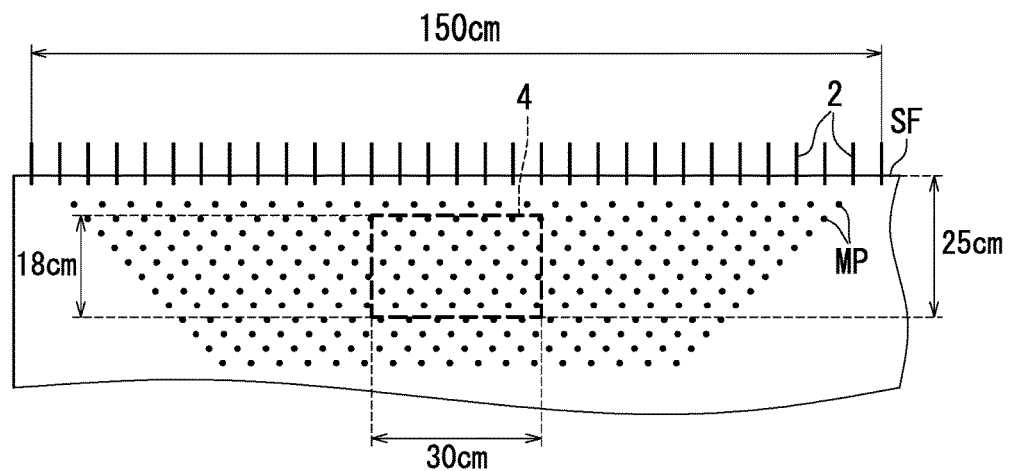

As illustrated in FIG. 5B, the water container 4 is buried at a location where the water (or the mixture of water and volcanic ash sandy soil) in the water container 4 is present in a depth range from 7 cm to 25 cm under the ground surface SF. Furthermore, the water container 4 is buried in the middle of a region having a width of 150 cm where the electrodes 2 of the moisture detecting apparatus 100 are buried. Moreover, the water container 4 is buried directly below the electrodes 2 so that the width direction of the water container 4 coincides with a direction in which the buried electrodes 2 are aligned. In other words, the water container 4 is buried such that a vertical plane that includes the electrodes 2 passes through the center of the water container 4 in the longitudinal direction thereof. Further, the measurement points MP in FIG. 5B each are a point at which the moisture detecting apparatus 100 measures a resistivity value $\rho$.

Figure 6:
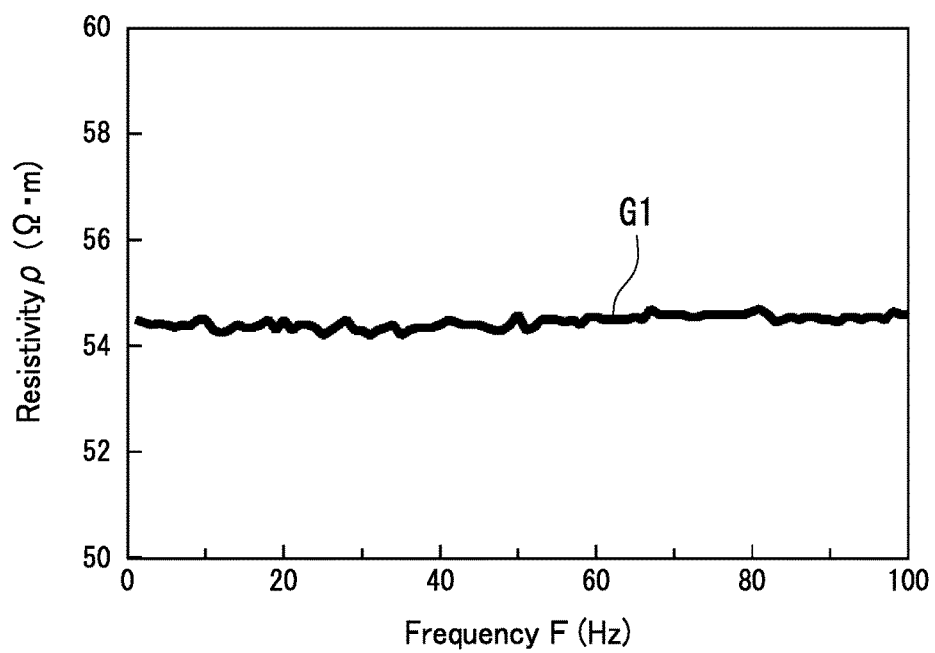
FIG. 6 is a graph representation indicating experiment results obtained in a situation in which water is put into the water container illustrated in FIG. 5A.

FIG. 6 indicates a graph G1 representing a result of an experiment performed in a situation in which water is put into the water container 4 illustrated in FIG. 5A. The horizontal axis represents frequency F (Hz) of an applied electric current. The vertical axis represents resistivity value $\rho$ ($\Omega \cdot m$) at a measurement point MP located the closest to the center of the water in the water container 4. As indicated by the graph G1, the resistivity value $\rho$ hardly varies even when the frequency F is changed from 1 Hz to 100 Hz.

Figure 7A:
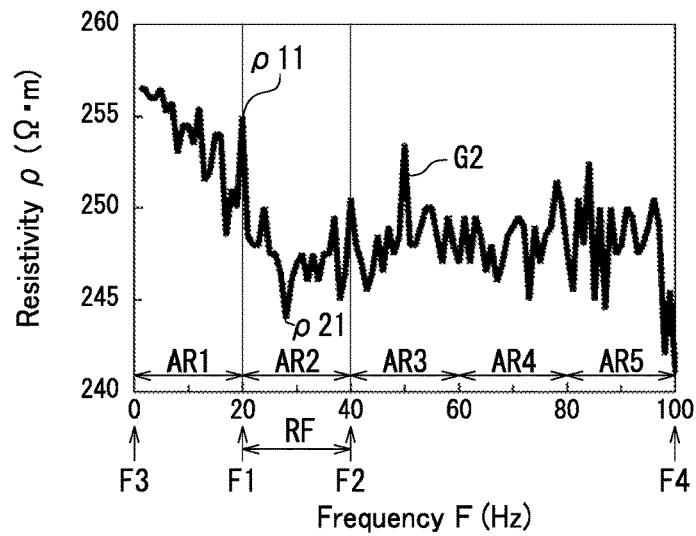
FIGS. 7A to 7C each are a graph representation indicating experiment results obtained in a situation in which water and volcanic ash sandy soil are put into the water container illustrated in FIG. 5A.
Figure 7B:
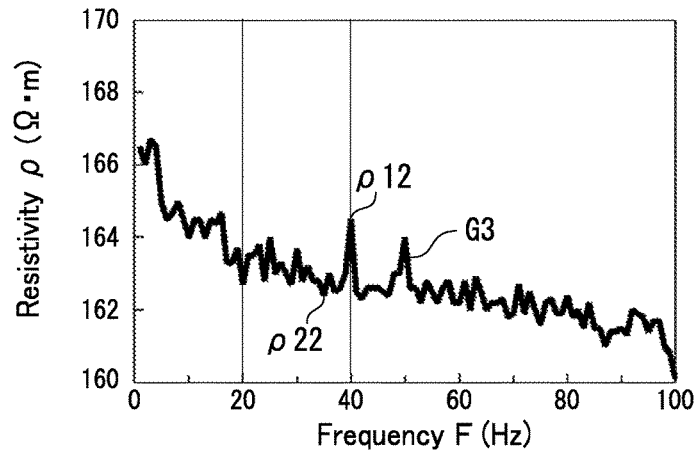
Figure 7C:
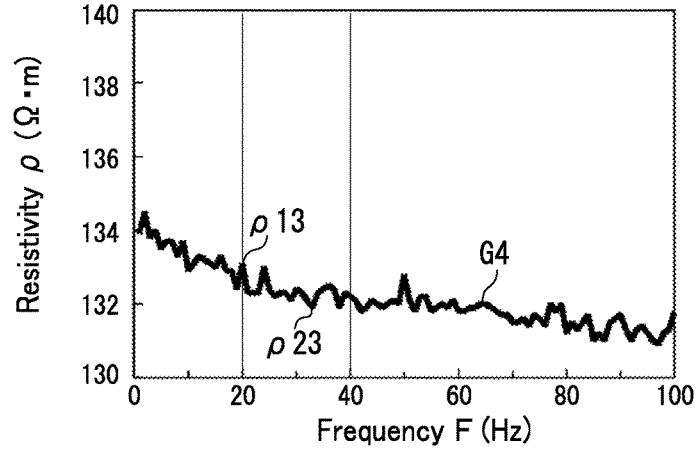

FIGS. 7A, 7B, and 7C each are a graph representation indicating a result of an experiment performed in a situation in which a mixture of water and volcanic ash sandy soil is put into the water container 4 illustrated in FIG. 5A. FIG. 7A indicates a result obtained in a situation in which the mixture has a moisture content of 60% (40% of volcanic ash sandy soil and 60% of water). FIG. 7B indicates a result obtained in a situation in which the mixture has a moisture content of 70% (30% of volcanic ash sandy soil and 70% of water). FIG. 7C indicates a result obtained in a situation in which the mixture has a moisture content of 80% (20% of volcanic ash sandy soil and 80% of water). Note that in each of FIGS. 7A, 7B, and 7C, the horizontal axis represents frequency F (Hz) of the applied current and the vertical axis represents resistivity value $\rho$ ($\Omega \cdot m$) at the measurement point MP located the closest to the center of the mixture in the water container 4, similarly to FIG. 6.

Comparison among the graph G1 in FIG. 6, a graph G2 in FIG. 7A, a graph G3 in FIG. 7B, and a graph G4 in FIG. 7C can find that variation of a graph in the vertical direction (dispersion) reduces as the moisture content is increased.

Furthermore, as indicated in for example FIG. 7A, the frequency range between 1 Hz and 100 Hz is divided into five frequency band zones AR1 to AR5. The deviation calculating section 164 illustrated in FIG. 2B calculates a standard deviation σk (k=1 to 5) in each of the frequency band zones ARk (k=1 to 5). Here, the calculated results are σ1=0.4431, σ2=0.6479, σ3=0.5990, σ4=0.5966, and σ5=0.3470. The standard deviation σ2 of the frequency band zone AR2 is a maximum. In the above situation, the frequency band selecting section 165 illustrated in FIG. 2B selects the frequency band FR2 (21 Hz to 40 Hz) corresponding to the frequency band zone AR2 of which standard deviation σ is a maximum as a frequency band FR2 for use in detecting moisture contained in the ground.

Furthermore, FIG. 7A indicates a maximum value ρ11 and a minimum value ρ21 among resistivity values ρ in the frequency band zone AR2. Similarly, FIG. 7B indicates a maximum value ρ12 and a minimum value ρ22 among resistivity values ρ in the frequency band zone AR2. FIG. 7C indicates a maximum value ρ13 and a minimum value ρ23 among resistivity values ρ in the frequency band zone AR2.

A quotient (ρ1/ρ2) obtained by dividing the maximum value ρ1 by the minimum value ρ2 among the resistivity values ρ in the frequency band zone AR2 is 1.045 in a situation in which the moisture content is 60% as in FIG. 7A, 1.012 in a situation in which the moisture content is 70% as in FIG. 7B, and 1.009 in a situation in which the moisture content is 80% as in FIG. 7C. As such, estimation can be made such that the smaller the quotient (ρ1/ρ2) obtained by dividing the maximum value ρ1 by the minimum value ρ2 among the resistivity values ρ is, the more moisture it can be estimated that the ground contains.

Figure 8A:
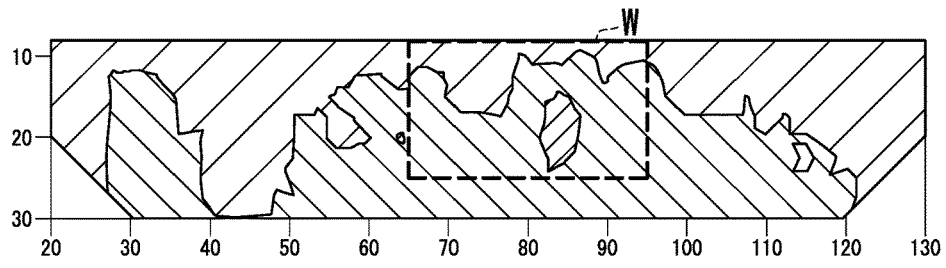
FIGS. 8A to 8F each are a graph representation indicating a standard deviation distribution in a frequency band in a situation in which water is put into the water container illustrated in FIG. 5A.
Figure 8B:
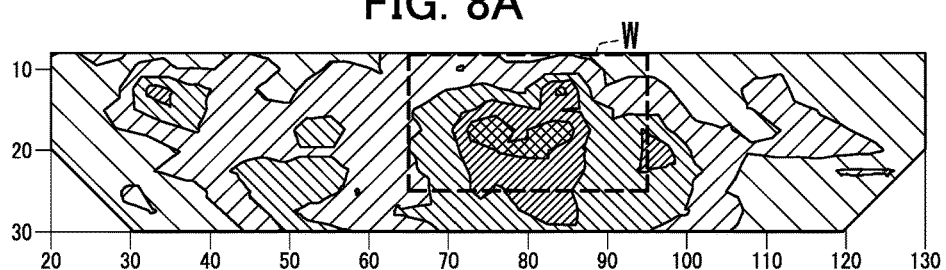
Figure 8C:
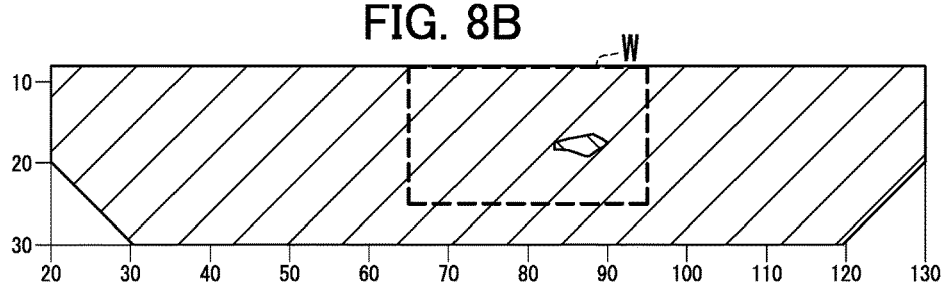
Figure 8D:
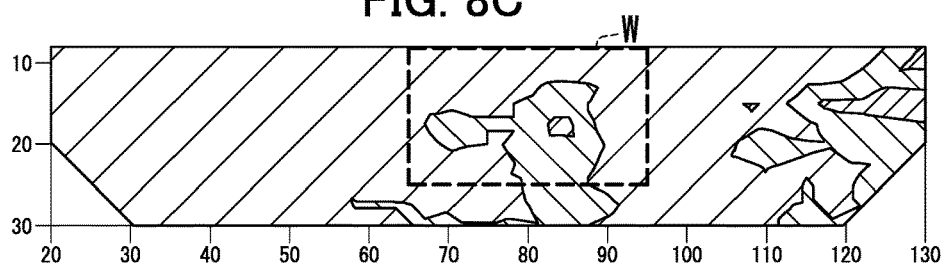
Figure 8E:
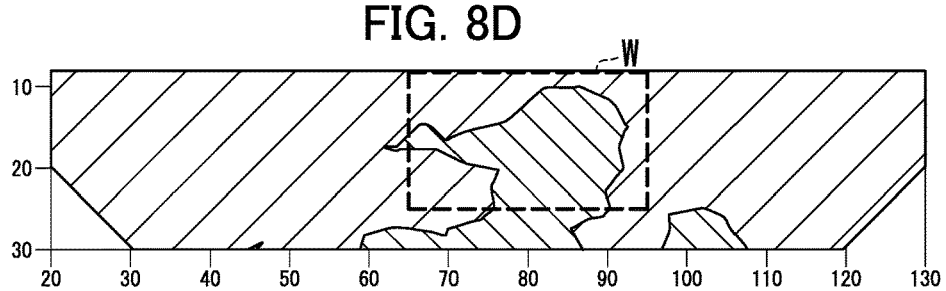
Figure 8F:
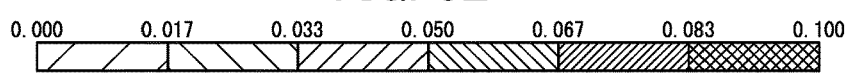

FIGS. 8A to 8F each indicate a standard deviation distribution in a frequency band in a situation in which sand gravel and water are put into the water container 4 illustrated in FIGS. 5A and 5B. FIG. 8A indicates a standard deviation distribution in a frequency band ranging from 1 Hz to 20 Hz. FIG. 8B indicates a standard deviation distribution in a frequency band ranging from 21 Hz to 40 Hz. FIG. 8C indicates a standard deviation distribution in a frequency band ranging from 41 Hz to 60 Hz. FIG. 8D indicates a standard deviation distribution in a frequency band ranging from 61 Hz to 80 Hz. FIG. 8E indicates a standard deviation distribution in a frequency band ranging from 81 Hz to 100 Hz. FIG. 8F indicates ranges of the standard deviation σ.

In each of FIGS. 8A-8E, the horizontal axis represents distance (cm) from a left end measurement point MP of the moisture detecting apparatus 100 in the width direction and the vertical axis represents depth (cm) of the measurement points MP of the moisture detecting apparatus 100. The respective standard deviation distributions in FIGS. 8A-8E indicate contour lines (lines that each connect measurement points MP having the same standard deviation 6) and hatching indicating the magnitude of the standard deviation σ. The distributions herein indicate that the darker the hatching is, the larger the standard deviation σ is.

Furthermore, a rectangle W in each of FIGS. 8A-8E represents the position of the water in the water container 4 illustrated in FIGS. 5A and 5B. Comparison among FIGS. 8A-8E can find that the standard deviation σ is especially large in a region inside the rectangle W in FIG. 8B and the location of the water is likely to be detected in the frequency band ranging between 21 Hz and 40 Hz. Note that the results show that the frequency band selecting section 165 illustrated in FIG. 2B appropriately performs frequency selection as a frequency band FR2 for use in detecting moisture contained in the ground. In other words, it shows that appropriate detection of moisture contained in the ground can be achieved through the frequency band selecting section 165 selecting the frequency band FR2 (21 Hz to 40 Hz) corresponding to the frequency band zone AR2 of which standard deviation σ is a maximum.

<Results of Demonstration of Effects of Moisture Detecting Apparatus>

Figure 9:
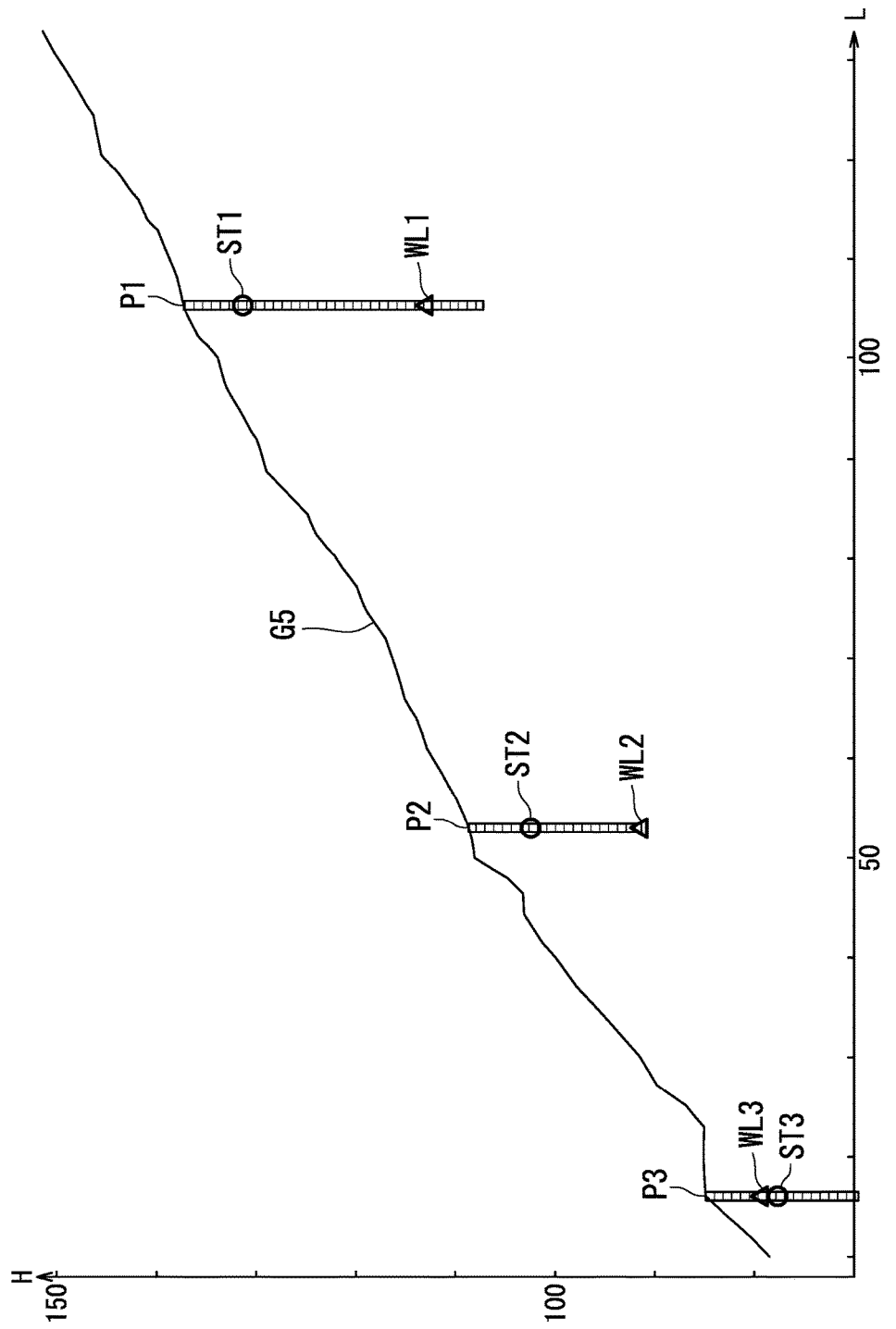
FIG. 9 is a graph representation indicating a main traverse line and results of boring at a location where demonstration was performed for demonstrating the effects of the moisture detecting apparatus illustrated in FIGS. 1A and 1B.
Figure 10:
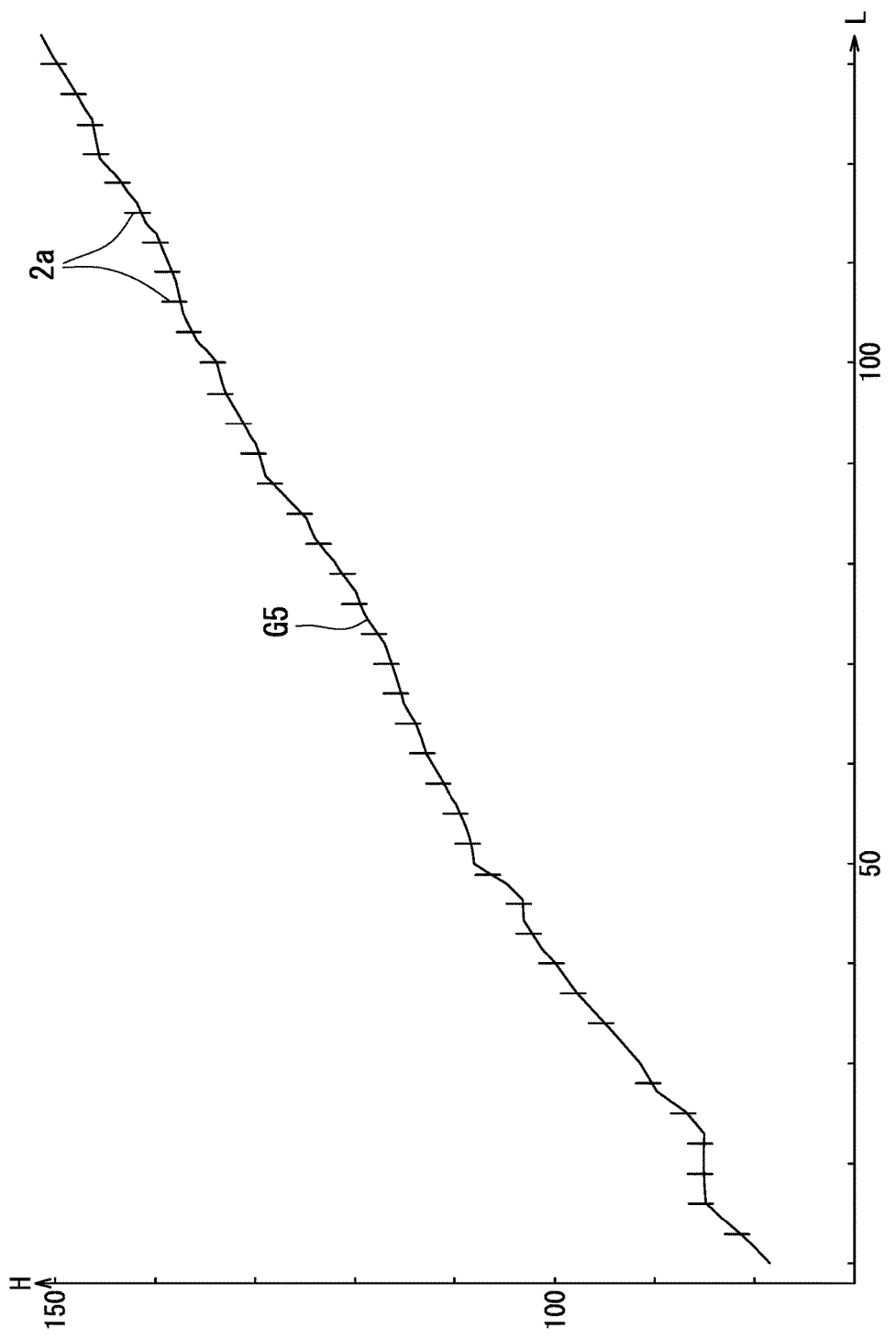
FIG. 10 is a graph representation indicating positions of respective electrodes arranged along the main traverse line illustrated in FIG. 9.
Figure 11:
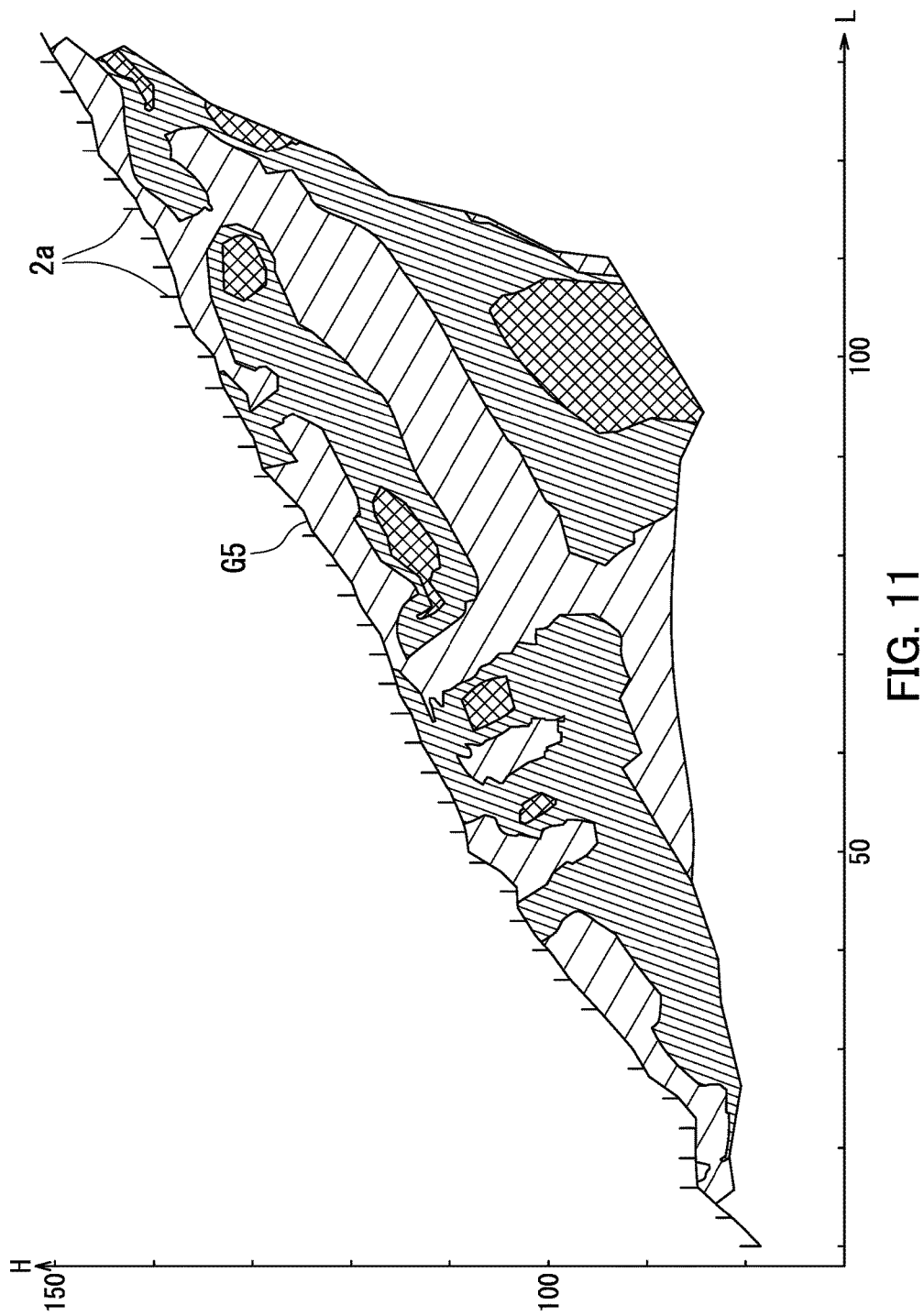
FIG. 11 is a graph representation indicating detection results (a standard deviation distribution) along the main traverse line in FIG. 9 obtained by the moisture detecting apparatus.

Description will be made next with reference to FIGS. 9 to 11 about results of demonstration of the effects of the moisture detecting apparatus 100 illustrated in FIGS. 1A and 1B. FIG. 9 is a graph representation indicating results of a boring survey and a main traverse line G5 in a place where demonstration of the effects of the moisture detecting apparatus 100 was performed. A horizontal axis represents distance L, and a vertical axis represents altitude H. Boring was performed at three points P1 to P3 along the main traverse line G5.

The boring survey was performed to measure maximum distortion amounts, distortion depths ST1 to ST3, and water levels WL1 to WL3. Specifically, boring to a depth of 30 m was performed at the point P1. In FIG. 9, circles (○) represent the distortion depths ST1 to ST3 at the respective bored points P1 to P3 and triangles (Δ) represent the respective water levels thereat. The distortion depth ST1 and the maximum distortion amount were 6 m and 200 μST, respectively, at the bored point P1. Also, the water level was located at a depth of 24.4 m. Boring to a depth of 17 m was performed at the point P2. The distortion depth ST2 and the maximum distortion amount were 6 m and 600 μST, respectively, at the bored point P2. Also, the water level was located at a depth of 16.9 m. Boring to a depth of 15 m was performed at the point P3. The distortion depth ST3 and the maximum distortion amount were 8 m and 150 μST, respectively, at the bored point P3. Also, the water level was located at a depth of 5.5 m.

It has been known that a landslide occurs at a distortion depth. By contrast, as described with reference to FIG. 9, locations of the distortion depths ST1 to ST3 were significantly different from the locations of the water levels WL1 to WL3, respectively. That is, it has been necessary to investigate whether or not any water layers had been present at any locations other than the locations of the water levels WL1 to WL3 obtained through the boring survey. In view of the foregoing, the inventors investigated locations where the water was present using the moisture detecting apparatus 100.

Next, an arrangement of electrodes 2a will be described with reference to FIG. 10. FIG. 10 is a graph representation indicating positions of the electrodes 2a arranged along the main traverse line G5. A horizontal axis represents distance L and a vertical axis represents altitude H. Fifty one electrodes 2a were arranged at intervals of 3 m along the main traverse line G5.

Description will be made next with reference to FIG. 11 about results of detection performed by the moisture detecting apparatus 100. FIG. 11 is a graph representation indicating the results of detection (distribution of standard deviations σ) along the main traverse line G5 performed by the moisture detecting apparatus 100. A horizontal axis represents distance L and a vertical axis represents altitude H. FIG. 11 indicates that the darker the hatching is, the larger the standard deviation σ is. As indicated in FIG. 11, it was found that a water layer was present in a depth range from 5 to 10 m from the ground level along the main traverse line G5. The results exhibited satisfactory agreement with the distortion depths ST1 to ST3. In other words, as a result of demonstration of the effects indicated in FIGS. 9 to 11, it was found that the moisture detecting apparatus 100 can appropriately detect moisture contained in the ground.

The present embodiment describes a configuration in which the frequency allotting section 161 performs frequency allotment at frequency intervals ΔF of 1 Hz. Note that it is preferable that the frequency allotting section 161 allots frequencies at intervals ΔF of no greater than 1 Hz. The smaller the frequency intervals ΔF are, the more appropriately the deviation calculating section 164 can calculate a standard deviation σ. Consequently, the frequency band selecting section 165 can select an appropriate frequency band. However, the respective processing times of the resistivity calculating section 162, the deviation calculating section 164, and the frequency band selecting section 165 increase as the frequency intervals ΔF are reduced.

Similarly, the shorter the frequency intervals ΔF are, the more appropriate values the estimation section 163 can obtain as a maximum value ρ1 and a minimum value ρ2. Consequently, the estimation section 163 can appropriately determine whether or not much moisture is contained.

The present embodiment describes a configuration in which the frequency allotting section 161 allots frequencies in a range between 1 Hz and 100 Hz. However, the range of frequencies that the frequency allotting section 161 allots is not limited to the aforementioned range. For example, the range may be between 1 Hz and 50 Hz or between 1 Hz and 200 Hz. An appropriate frequency band is likely to be selected by the frequency band selecting section 165 as the range of frequencies that the frequency allotting section 161 allots is increased.

The present embodiment describes a configuration in which the deviation calculating section 164 divides the range between the third frequency F3 and the fourth frequency F4 into the five frequency band zones ARk. However, it is only required that the deviation calculating section 164 divides the range into a plurality of frequency band zones. An appropriate selected frequency band is likely to be obtained as the number of divided frequency band zones is increased. However, the respective processing times of the deviation calculating section 164 and the frequency band selecting section 165 increases as the number of divided frequency band zones is increased. In a configuration in which the number of divided frequency band zones is too large, the number of frequencies in each of the frequency band zones among the frequencies allotted by the frequency allotting section 161 is small, thereby disabling appropriate calculation of the standard deviations 6. It is necessary to determine the number of divided frequency band zones so that the number of frequencies in each frequency band zone is for example at least 10.

The embodiment of the present invention has been described so far with reference to the drawings (FIGS. 1A to 11). Note that the present invention is not limited to the embodiment described above and various alterations can be made within the scope not departing from the gist of the present invention.

The drawings are schematic illustrations that emphasize elements of configuration in order to facilitate understanding thereof. Therefore, in order that elements of configuration can be easily illustrated, dimensions such as thickness and length of each of the elements in the drawings may differ from the actual dimensions thereof.

INDUSTRIAL APPLICABILITY

The present invention can is applicable to a moisture detecting apparatus, a moisture detecting method, and a moisture detection program for detecting moisture in the ground.

REFERENCE SINGS LIST

- 100 moisture detecting apparatus
- 1 moisture detection device main body
- 11 direct current stabilizing power supply
- 12 oscillator
- 13 rectangular wave drive circuit
- 14 electrode switching circuit
- 15 data logger
- 16 computer
- 161 frequency allotting section (frequency allotting means)
- 162 resistivity calculating section (resistivity calculating means)
- 163 estimation section (estimation means)
- 164 deviation calculating section (deviation calculating means)
- 165 frequency band selecting section (frequency band selecting means)
- 2 electrode
- 21, 22 pair of current electrodes
- 23, 24 pair of potential electrodes
- 3 lead wire
- 4 water container

The invention claimed is:

1. A moisture detecting apparatus that detects moisture contained in a predetermined region of a ground, comprising:

plural pairs of current electrodes each configured to measure a current value of an alternating current input to the predetermined region;

plural pairs of potential electrodes each configured to measure a voltage value corresponding to the alternating current;

a frequency allotting means configured to allot a plurality of frequencies at specific frequency intervals in a range between a preset first frequency and a second present frequency higher than the first frequency to a frequency of the alternating current;

a resistivity calculating means configured to calculate a resistivity value in the predetermined region using the current value and the voltage value each time a frequency is allotted by the frequency allotting means; and an estimation means configured to obtain a maximum value and a minimum value among resistivity values obtained through calculation by the resistivity calculating means, to obtain a quotient obtained by dividing the maximum value by the minimum value, and to perform estimation such that the smaller the quotient is, the more moisture the predetermined region contains.

2. The moisture detecting apparatus according to claim 1, wherein the specific frequency intervals each are no greater than 1 Hz, and the frequency allotting means allots at least ten frequencies.

3. The moisture detecting apparatus according to claim 1, wherein the frequency allotting means allots a plurality of frequencies at the specific frequency intervals in a range between a third frequency lower than the first frequency and a fourth frequency higher than the second frequency, and the moisture detecting apparatus further comprises:

a deviation calculating means configured to divide the range between the third frequency and the fourth frequency into two or more frequency band zones and calculate, in each of the frequency band zones, a standard deviation of the resistivity values obtained through calculation by the resistivity calculating means; and a frequency band selecting means configure to select, as a frequency band for use in detecting moisture contained in the ground, a frequency band corresponding to one of the frequency band zones of which standard deviation is a maximum among standard deviations obtained through calculation by the deviation calculating means.

4. The moisture detecting apparatus according to claim 3, wherein
the first frequency is a lower limit frequency of the frequency band selected by the frequency selecting means, and
the second frequency is an upper limit frequency of the frequency band selected by the frequency band selecting means.

5. The moisture detecting apparatus according to claim 1, wherein
the first frequency is approximately 20 Hz and the second frequency is approximately 40 Hz.

6. The moisture detecting apparatus according to claim 1, wherein
the alternating current has a rectangular wave form.

7. The moisture detecting apparatus according to claim 1, wherein
the estimation means performs the estimation such that
when the quotient is equal to or smaller than a threshold value, the predetermined region is moist, and
when the quotient is larger than the threshold value, the predetermined region is less moist than when the quotient is equal to or larger than the threshold value.

8. A moisture detecting apparatus that detects moisture contained in a predetermined region of a ground, comprising:
plural pairs of current electrodes each configured to measure a current value of an alternating current input to the predetermined region;
plural pairs of potential electrodes each configured to measure a voltage value corresponding to the alternating current;
a frequency allotting means configured to allot a plurality of frequencies at specific frequency intervals in a range between a preset third frequency and a fourth frequency higher than the third frequency to a frequency of the alternating current;
a resistivity calculating means configured to calculate a resistivity value in the predetermined region using the current value and the voltage value each time a frequency is allotted by the frequency allotting means;
a deviation calculating means configured to divide the range between the third and fourth frequencies into two or more frequency band zones and calculate, in each of the frequency band zones, a standard deviation of resistivity values obtained through calculation by the resistivity calculating means; and
a frequency band selecting means configured to select, as a frequency for use in detection of moisture contained in the ground, a frequency band corresponding to one of the frequency band zones of which standard deviation is a maximum among standard deviations obtained through calculation by the deviation calculating means.

9. A moisture detecting method using a moisture detecting apparatus that detects moisture contained in a predetermined region of a ground, the moisture detecting apparatus including plural pairs of current electrodes that each measure a current value of an alternating current input to the predetermined region and plural pairs of potential electrodes that each measure a voltage value corresponding to the alternating current, the method comprising:
allotting a plurality of frequencies at specific frequency intervals in a range between a preset first frequency and a second frequency higher than the first frequency to a frequency of the alternating current;
calculating a resistivity value in the predetermined region using the current value and the voltage value each time a frequency is allotted in the allotting a plurality of frequencies; and
obtaining a maximum value and a minimum value among resistivity values obtained through the calculating a resistivity value, obtaining a quotient obtained by dividing the maximum value by the minimum value, and performing estimation such that the smaller the quotient is, the more moisture the predetermined region contains.

10. The moisture detecting method according to claim 9, wherein
in the allotting a plurality of frequencies, a plurality of frequencies are allotted at the specific frequency intervals in a rage between a third frequency lower than the first frequency and a fourth frequency higher than the second frequency, and
the method further comprises:
dividing the range between the third and fourth frequencies into two or more frequency band zones and calculating, in each of the frequency band zones, a standard deviation of the resistivity values obtained through the calculating a resistivity value; and
selecting, as a frequency for use in detection of moisture contained in the ground, a frequency band corresponding to one of the frequency band zones of which standard deviation is a maximum among standard deviations obtained through the calculating a standard deviation.

11. The moisture detecting method according to claim 9, wherein
in the obtaining, the estimation is performed such that
when the quotient is equal to or smaller than a threshold value, the predetermined region is moist, and
when the quotient is larger than the threshold value, the predetermined region is less moist than when the quotient is equal to or larger than the threshold value.

12. A moisture detecting method using a moisture detecting apparatus that detects moisture contained in a predetermined region of a ground, the moisture detecting apparatus including plural pairs of current electrodes that each measure a current value of an alternating current input to the predetermined region and plural pairs of potential electrodes that each measure a voltage value corresponding to the alternating current, the method comprising:
allotting a plurality of frequencies at specific frequency intervals in a range between a preset third frequency and a fourth frequency higher than the third frequency to a frequency of the alternating current;
calculating a resistivity value in the predetermined region using the current value and the voltage value each time a frequency is allotted in the allotting a plurality of frequencies;
dividing the range between the third and fourth frequencies into two or more frequency band zones and calculating, in each of the frequency band zones, a standard deviation of resistivity values obtained through the calculating a resistivity value; and selecting, as a frequency for use in detection of moisture contained in the ground, a frequency band corresponding to one of the frequency band zones of which standard deviation is a maximum among standard deviations obtained through the calculating a deviation.

13. A non-transitory computer readable storage medium that stores therein a moisture detection program for a moisture detecting apparatus that detects moisture contained in a predetermined region of a ground, the moisture detecting apparatus including plural pairs of current electrodes that each measure a current value of an alternating current input to the predetermined region, plural pairs of potential electrodes that each measure a voltage value corresponding to the alternating current, and a computer, wherein the program causes the computer to function as:

a frequency allotting means configured to allot a plurality of frequencies at specific frequency intervals in a range between a preset first frequency and a second frequency higher than the first frequency to a frequency of the alternating current;

a resistivity calculating means configured to calculate a resistivity value in the predetermined region using the current value and the voltage value each time a frequency is allotted by the frequency allotting means; and an estimation means configured to obtain a maximum value and a minimum value among resistivity values obtained through calculation by the resistivity calculating means, to obtain a quotient obtained by dividing the maximum value by the minimum value, and to perform estimation such that the smaller the quotient is, the more moisture the predetermined region contains.

14. The non-transitory computer readable storage medium according to claim 13, wherein the frequency allotting means allots a plurality of frequencies at the specific frequency interval in a range between a third frequency lower than the first frequency and a fourth frequency higher than the second frequency, and the program further causes the computer to function as:

a deviation calculating means configured to divide the range between the third and fourth frequencies into two or more frequency band zones and calculate, in each of the frequency band zones, a standard deviation of the resistivity values obtained through calculation by the resistivity calculating means; and a frequency band selecting means configured to select, as a frequency for use in detection of moisture contained in the ground, a frequency band corresponding to one of the frequency band zones of which standard deviation is a maximum among standard deviations obtained through calculation by the deviation calculating means.

15. The non-transitory computer readable storage medium according to claim 13, wherein the estimation means performs the estimation such that
when the quotient is equal to or smaller than a threshold value, the predetermined region is moist, and
when the quotient is larger than the threshold value, the predetermined region is less moist than when the quotient is equal to or larger than the threshold value.

16. A non-transitory computer readable storage medium that stores therein a moisture detection program for a moisture detecting apparatus that detects moisture contained in a predetermined region of a ground, the moisture detecting apparatus including plural pairs of current electrodes that each measure a current value of an alternating current input to the predetermined region, plural pairs of potential electrodes that each measure a voltage value corresponding to the alternating current, and a computer, wherein the program causes the computer to function as:

a frequency allotting means configured to allot a plurality of frequencies at specific frequency intervals in a range between a preset third frequency and a fourth frequency higher than the third frequency to a frequency of the alternating current;

a resistivity calculating means configured to calculate a resistivity value in the predetermined region using the current value and the voltage value each time a frequency is allotted by the frequency allotting means;

a deviation calculating means configured to divide the range between the third and fourth frequencies into two more frequency band zones and calculate, in each of the frequency band zones, a standard deviation of resistivity values obtained through calculation by the resistivity calculating means; and a frequency band selecting means configured to select, as a frequency for use in detection of moisture contained in the ground, a frequency band corresponding to one of the frequency band zones of which standard deviation is a maximum among standard deviation obtained through calculation by the deviation calculating means.

* * * * *